(12) United States Patent
Barnes et al.

(10) Patent No.: US 10,557,793 B1
(45) Date of Patent: Feb. 11, 2020

(54) SCANNING MICROSCOPE USING A PROBE BEAM DEFLECTION TECHNIQUE (PBDT)

(71) Applicant: Government of the United States, as represented by the Secretary of the Air Force, Wright-Patterson AFB, OH (US)

(72) Inventors: Ronald A. Barnes, New Braunfels, TX (US); Hope T. Beier, San Antonio, TX (US); Bennett L. Ibey, San Antonio, TX (US); Caleb C Roth, San Antonio, TX (US); Joel N Bixler, San Antonio, TX (US); Christopher M Valdez, San Antonio, TX (US)

(73) Assignee: United States of America as represented by the Secretary of the Air Force, Wright Patterson, AFB, OH (US)

(*) Notice: Subject to any disclaimer, the term of this patent is extended or adjusted under 35 U.S.C. 154(b) by 55 days.

(21) Appl. No.: 16/058,466

(22) Filed: Aug. 8, 2018

Related U.S. Application Data

(60) Provisional application No. 62/546,309, filed on Aug. 16, 2017.

(51) Int. Cl.
*G01N 21/41* (2006.01)
*G01N 21/21* (2006.01)
(Continued)

(52) U.S. Cl.
CPC ......... *G01N 21/4133* (2013.01); *G01N 21/21* (2013.01); *G02B 21/006* (2013.01);
(Continued)

(58) Field of Classification Search
CPC ............... G01N 21/4133; G01N 21/21; G02B 21/0032; G02B 21/0036; G02B 21/006; G02B 21/0068; G02B 21/008
See application file for complete search history.

(56) References Cited

U.S. PATENT DOCUMENTS 2,601,175 A 6/1952 Smith
4,097,739 A 6/1978 Muller et al.
(Continued)

OTHER PUBLICATIONS

Maswadi et al., "All-optical optoacoustic microscopy based on probe beam deflection technique," Photoacoustics 4, pp. 91-101, Feb. 24, 2016.
(Continued)

*Primary Examiner* — Jamil Ahmed
(74) *Attorney, Agent, or Firm* — AFMCLO/JAZ; David Franklin

(57) ABSTRACT

Variations in a translucent medium are imaged by detecting deflections and/or polarization shifts in a probe beam transmitted through the translucent medium. Deflections and polarization shifts may be detected using a first polarizing filter positioned between a probe beam generator and the translucent medium to polarize the probe beam in a first direction, a beam splitter positioned to receive the probe beam after it has been transmitted through the medium, and a probe beam deflection detector that receives a first split beam and provides a deflection signal associated with refractive index variations in the medium. A second polarizing filter receives a second split beam and polarizes it in a second direction, perpendicular to the first direction. An intensity sensor receives the second split beam, after it has passed through the second polarizing filter, and provides an intensity signal associated with a polarization shift in the medium.

21 Claims, 4 Drawing Sheets

(51) Int. Cl.
    *G02B 21/06* (2006.01)
    *G02B 21/00* (2006.01)
(52) U.S. Cl.
    CPC ....... *G02B 21/008* (2013.01); *G02B 21/0032* (2013.01); *G02B 21/0036* (2013.01); *G02B 21/0068* (2013.01)

(56) References Cited

U.S. PATENT DOCUMENTS

| | | | |
|---|---|---|---|
| 6,041,020 A | 3/2000 | Caron et al. | |
| 2012/0002193 A1 | 1/2012 | Elliott et al. | |
| 2013/0041247 A1 | 2/2013 | Maswadi | |
| 2014/0330097 A1* | 11/2014 | Weiss | A61B 5/1455 600/316 |

OTHER PUBLICATIONS

Ronald A. Barnes, Jr., Saher Maswadi, Randolph Glickman, and Mehdi Shadaram, "Probe beamdeflection technique as acoustic emission directionality sensor with photoacoustic emission source," Jan. 20, 2014/vol. 53, No. 3/Applied Optics.

Roth, Caleb C. et al. "Characterization of Pressure Transients Generated by Nanosecond Electrical Pulse (nsEP) Exposure." Scientific Reports 5 (2015): 15063. PMC. Web. Aug. 15, 2017.

* cited by examiner

SCANNING MICROSCOPE USING A PROBE BEAM DEFLECTION TECHNIQUE (PBDT)

CROSS-REFERENCE TO RELATED APPLICATION

This application claims the benefit of U.S. Provisional Application No. 62/546,309 filed Aug. 16, 2017, where the entire content of the foregoing application is hereby incorporated by reference.

STATEMENT OF GOVERNMENT INTEREST

The invention described herein may be manufactured, used, and licensed by or for the Government of the United States for all governmental purposes without the payment of any royalty.

BACKGROUND

In cancer research, defense applications, and other areas, directed energy is utilized to induce a biological response in a material both in-vivo and in-vitro. Biological responses include induced cell apoptosis, DNA transfection, exciting and inhibiting neuron action potentials, etc. Imaging of the spatial and temporal response to directed energy provides information to improve the delivery of directed energy impulses, through an enhanced understanding of the driving mechanisms responsible for a desired biological response. This will increase the effectiveness of directed energy cancer treatment, and the effectiveness of non-lethal weapons system.

Currently, all optical methods for high spatial resolution, fast (<100 ns) imaging of mechanical phenomena in high strength electric fields are limited to pump probe photography (PPP) and Schlieren imaging. PPP and Schlieren photography are based on the deflection of a laser beam as it travels through a medium of interest. However, these methodologies require short pulsed lasers with pulse durations less than 20 ns and cameras with high contrast and time resolution to achieve the necessary time resolution and contrast required to image multi-physics phenomena, such as mechanically induced refractive index gradients.

In the past, the Kerr effect has been utilized to map electric field distributions in liquids. The Kerr effect is the polarization shift of an optical beam, due to the alignment of water molecules acting as a crystal when exposed to an external electric field. For example, the electric field distribution has been mapped in non-conductive media during the study of pre-breakdown phenomena.

However, the combination of deflection based imaging and Kerr effect imaging to characterize directed energy dosimetry achieving micron spatial resolution and sub-nanosecond time resolution has not been demonstrated.

The probe beam deflection technique (PBDT) correlates the deflection of a laser beam propagating through a medium of interest with any detectable thermal or acoustic disturbance in the media. PBDT and PPP both require a repetitive/stable event to image a time-lapse sequence, however unlike PPP, PBDT does not require a short pulse laser to illuminate a camera aperture to acquire an image. PBDT has been utilized previously for ultrasound and photoacoustic measurement, as well as imaging. The technique has been applied to the measurement of acoustic waves in gas phase, namely the gas coupled laser acoustic detector (GCLAD), where detection bandwidth is limited by the speed of sound in air. PBDT has also been shown to be a passive wide band ultrasonic sensor in liquids. Imaging of an ultrasonic target, such as soft tissue, has been demonstrated in photo-acoustics, and imaging of a photoacoustic wave has been shown. In addition, PBDT has been used to measure acoustic waves generated by a nanosecond electric pulse (nsEP) in one-dimension.

Currently, no systems or techniques are available for measuring both mechanical and electromagnetic responses of a medium to a directed energy pulse.

BRIEF DESCRIPTION OF THE DRAWINGS

The accompanying drawings provide visual representations which will be used to more fully describe various representative embodiments and can be used by those skilled in the art to better understand the representative embodiments disclosed and their inherent advantages. The drawings are not necessarily to scale, emphasis instead being placed upon illustrating the principles of the devices, systems, and methods described herein. In these drawings, like reference numerals may identify corresponding elements.

DETAILED DESCRIPTION

Figure 1:
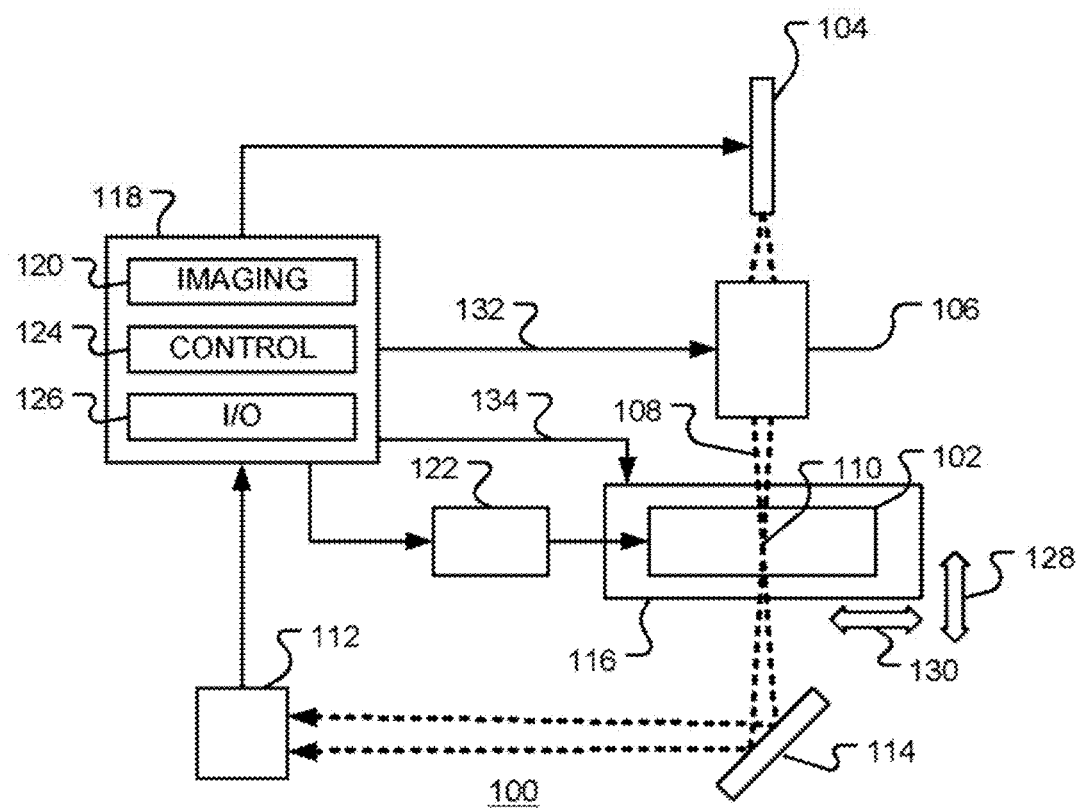
FIG. 1 is a block diagram of a scanning microscope, in accordance with a representative embodiment.

The various methods, systems, apparatuses, and devices described herein apply generally to spatial and temporal imaging of mechanical and electromagnetic phenomena in a medium using a scanning microscope and a probe beam deflection technique (PBDT).

In one embodiment, PBDT utilizes a continuous wave (CW) laser beam that illuminates a small portion of an entire imaging plane of a medium to be scanned. The deflection of the probe beam, resulting from refractive index changes of the media, is resolved via a quadrature photodiode or other deflection sensor, where the deflection sensor has a time resolution less than a nanosecond. The beam is moved in a scan pattern such that each beam position corresponds to a single pixel of an image, and a single temporal sample of the signal acquired at that pixel corresponds to a single pixel time lapse frame. This results in a time-lapse image having 1 ns or less time resolution. This technique provides an improvement over pump probe photography (PPP) and Schlieren photography in both time resolution and also in image contrast, since the laser beam can be focused into a small interaction area thereby amplifying the deflection of the beam and increasing signal to noise ratio (SNR) at the detector. Both mechanical and thermal images can be acquired simultaneously which is not possible with technologies such as forward-looking infrared (FLIR) cameras.

While this invention is susceptible of being embodied in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals may be used to describe the same, similar or corresponding parts in the several views of the drawings.

In this document, relational terms such as first and second, top and bottom, and the like may be used solely to distinguish one entity or action from another entity or action without necessarily requiring or implying any actual such relationship or order between such entities or actions. The terms "comprises," "comprising," "includes," "including," "has," "having," or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference throughout this document to "one embodiment," "certain embodiments," "an embodiment," "implementation(s)," "aspect(s)," or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C." An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

All documents mentioned herein are hereby incorporated by reference in their entirety. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

In the following description, it is understood that terms such as "first," "second," "top," "bottom," "up," "down," "above," "below," and the like, are words of convenience and are not to be construed as limiting terms. Also, the terms apparatus and device may be used interchangeably in this text.

In general, the devices, systems, and methods described herein relate to a scanning microscope that utilizes a probe beam deflection technique (PBDT). The microscope is a beam deflection based microscope that can be utilized to resolve refractive index gradients induced by various physics phenomena. The microscope may be used, for example, in directed energy (DE) applications applied to biology in-vitro, to induce a wide variety of dynamics including mechanical, thermal, electrochemical and electrodynamic. In order to correlate the observed biological response resulting from directed energy exposure with the driving mechanism, it is desirable to quantify and image each physical phenomena induced by the exposure. The PBDT microscope may be used as a multi-physics dosimeter, with sub-micron spatial resolution and nanosecond time resolution, and may be used to identify the relationships between a driving mechanism for directed energy applications and a resulting biological response.

FIG. 1 is a block diagram of a scanning microscope 100 utilizing a PBDT. The microscope 100 is used for measuring temporal and/or spatial variations in a translucent medium 102, and includes a light source 104, such as a laser, and a lens system 106, such as a microscope objective lens, for focusing light from the light source. The focused light is used as a probe beam 108 that is focused at a first location 110 in the translucent medium 102. A probe beam deflection detector 112 is located to detect the probe beam after it has been transmitted through the translucent medium 102. In the example configuration, the probe beam is directed to the deflection detector 112 using mirror 114, but other optical paths may be used. Probe beam deflection detector 112 is configured to provide one or more deflection signals dependent upon refractive index variations in the translucent medium 102. A scan stage 116 is configured to move the first location in a scan pattern comprising one or more scan locations. In this example, scan stage 116 moves translucent medium 102. However, other embodiments may move the lens system 106. Still further configurations will be apparent to those of ordinary skill in the art. In general, the relative location of the translucent medium and the lens system are moved according to a scan pattern.

Processor 118 includes an image processing module 120 that is operable to produce an image of temporal or spatial variations in the translucent medium dependent upon the one or more deflection signals and the one or more scan locations. The image processing module may comprise, for example, software executed on the processor, custom hardware, or a combination thereof. The image processing module 120 may be part of an integrated system, or may be a separate element at a local or remote location. Translucent medium 102, such as a biological material, may be excited by a directed energy source 122. The directed energy source 122 may be a nanosecond electric pulse (nsEP) generator or a pulsed power generator, for example. In the embodiment shown, processor 118 also includes a control module 124, for controlling scan stage 116, light source 104, and directed energy source 122. The processor 118 also includes an input/output (I/O) module 126. I/O module 126 may provide a user interface, such as a graphical user interface for displaying images and an input for user commands. In addition, I/O module 126 may provide for storage or transfer of sensed signals or computed images. Modules 120, 124 and 126 may be combined in a single processor or distributed between two or more processors. In addition, the image processing module 120 and I/O module 126 may be at remote locations.

Lens system 106 is used to focus the probe beam 108 at a scan location 110 in the translucent medium 102. As depicted by arrow 132, the focal length of the lens system may be varied under the control of control module 124 so as to vary the scan location. Alternatively, the scan location 110 may be varied by adjusting the scan stage 116 in the vertical Y-direction (Z-direction) as indicated by arrow 128. The scan stage may also be used to adjust the scan location horizontally (X- and Y-directions) as indicated by arrow 130. Movement of scan stage 116 may be performed under control of control module 124, as depicted by arrow 134.

In accordance with an aspect of the present disclosure, the PBDT microscope includes a means, such as a lens or lens system, for focusing the laser beam. Focusing the laser beam creates a spatially bandlimited point sensor. The bandwidth of PBDT is proportional to the beam waist of the beam, if the beam is focused This bandwidth is highest at the focal point and reduces rapidly outside of the focal plane. As a result, most of the measurable deflection in the probe beam occurs close to the focus and refractive index changes occurring close to the focal plane will dominate the deflection measurement. Thus, focusing the laser beam provides an ability to scan in the vertical direction (Z-direction), that is, along the propagation axis of the laser beam. In addition, the PBDT microscope can scan in an X-Y plane transverse to the propagation axis.

The PBDT microscope 100 is a passive optical sensing system and may be used to detect refractive index gradients, in a medium 102 in a gas or liquid phase, with micron spatial resolution and nanosecond temporal resolution. Refractive index gradients may be induced by a variety of phenomena including: mechanical, thermal, and electrochemical dynamics. As the probe beam emitted from the lens system 106 traverses a refractive index gradient, the beam deflects and the deflection can be quantified with deflection detector 112, which may be a bisectional or quadrature photodiode, for example.

In one embodiment, light source 104 comprises a helium-neon (HeNe) continuous wave (CW) laser source. In one embodiment, the laser source may have a power of 22 mW. However, lasers with greater or less power may be used.

Scan stage 116 has one or more degrees of positionable freedom. In one embodiment, scan stage 116 comprises a set of X-Y-Z stages with minimum 500 nm step resolution.

In one embodiment, deflection detector 112 comprises a pair of silicon photodiode detectors with adjustable gain from 0 dB to 50 dB and a time resolution of less than 1 ns at 0 dB.

The microscope 100 may include other optical components such as mirrors, lenses and beam splitters and may provide a spatial resolution of less than 10 μm together with a sub-nanosecond time resolution.

Image contrast in a resulting image is dependent upon the spot size of the focused probed beam, the power of the laser, and the sensitivity of the deflection detector 110.

Figure 2:
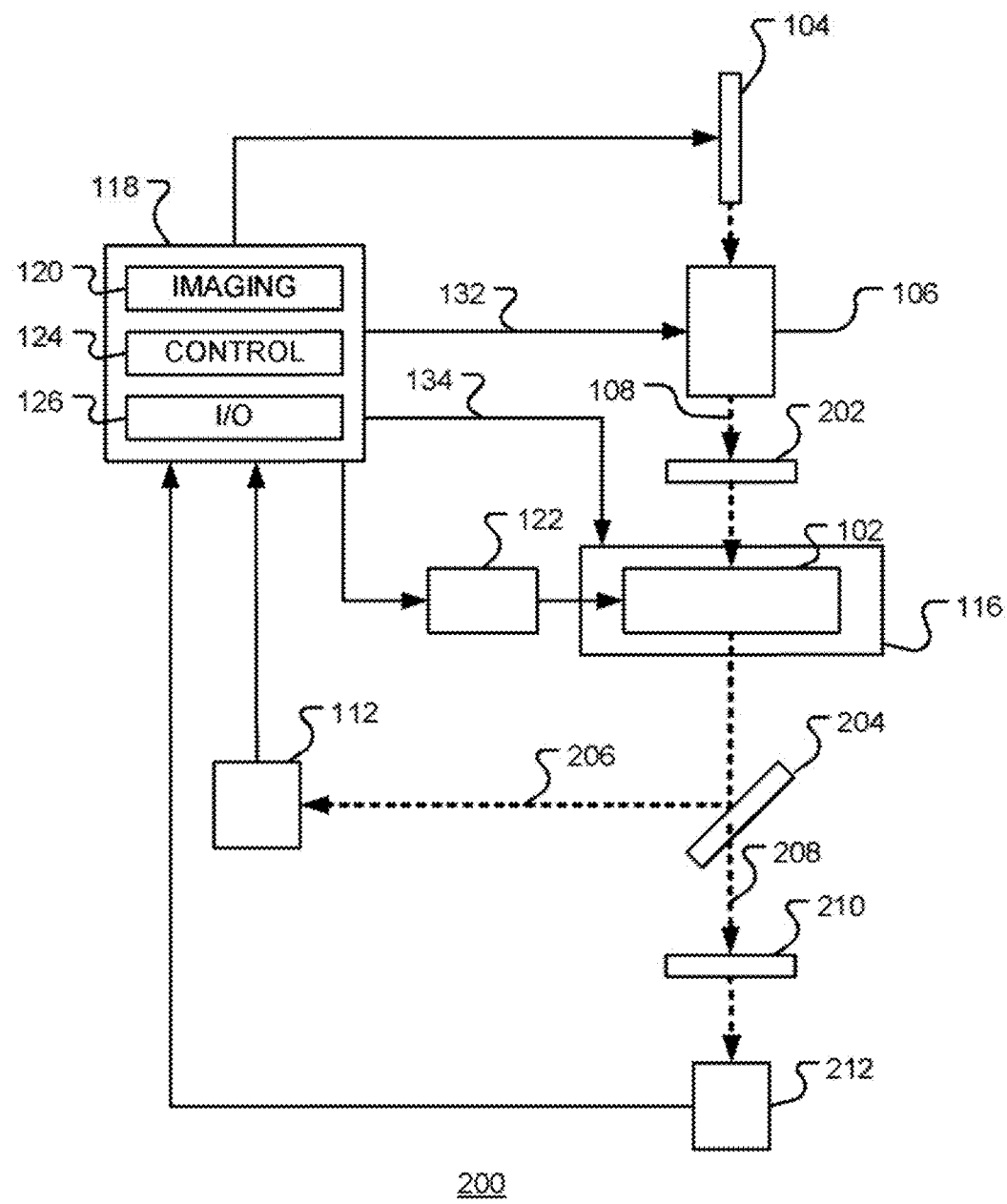
FIG. 2 is a block diagram of a scanning microscope, in accordance with a further representative embodiment.

FIG. 2 is a block diagram of a scanning microscope 200 consistent with further embodiments of the disclosure. In this embodiment, scanning microscope 200 is configured to enable sensing of polarization shifts in medium 102. The electric vector associated with a light vibrates in a plane perpendicular to the direction of propagation. Probe beam 108 is polarized in first polarizing filter 202 before traversing translucent medium 102. First polarizing filter 202 is positioned between the lens system 106 and the translucent medium 102 and is configured to polarize the probe beam so that the electric vector vibrates in a first direction only. The first direction is indicated by arrow 214. As light passes through the translucent medium, the direction of polarization may be altered. Beam splitter 204 is positioned to receive the probe beam after it has been transmitted through the translucent medium 102. Beam splitter 204 splits the received probe beam into a first split beam 206 and second split beam 208, where the first split beam 206 is incident upon the probe beam deflection detector 112. Second polarizing filter 210 is positioned to receive the second split beam 208 and is oriented to polarize the second split beam in a second direction (not shown), perpendicular to the first direction. In the example shown, the first direction is indicated by arrow 214, while the second direction is perpendicular to both the first direction 214 and the direction of propagation of the probe beam. If the probe beam is unaltered by passage through the translucent medium, all of the light will be filtered out by the second polarizing filter, since the light has not component in the second direction. However, if the polarization of the probe beam is altered, and contains a component in the second direction, then some light will pass through the second polarizing filter. Intensity sensor 212 is positioned to receive the second split beam after it has passed through the second polarizing filter 210. The intensity sensor provides an intensity signal dependent upon a polarization shift in the translucent medium. When the medium produces no polarization shift, the combination of the first and second polarizing filter blocks all of the probe beam. Signals from the intensity sensor are passed to the image processing module 120 of processor 118, which is operable to produce an image of temporal or spatial variations in the translucent medium dependent upon the intensity signal and the scan locations.

The combination of first polarizing filter 202, second polarizing filter 210 and intensity sensor 212 enables the detection of polarization shifts as the probe beam 108 passes through the translucent medium 102. For example, polarization shifts resulting from the Kerr effect enable the detection of electric field magnitudes. The combination of PBDT and Kerr effect sensing in scanning microscope 200 makes it possible to produce images of multi-physics phenomena (such as mechanically or thermally induced refractive index gradients and polarization shifts caused by electric field distributions) resulting from directed energy stimulus in-vitro and to correlate the driving mechanism with the observed biological response. This is not possible with technologies such as forward-looking infrared (FLIR) cameras that rely on emitted infra-red radiation alone.

Figure 3:
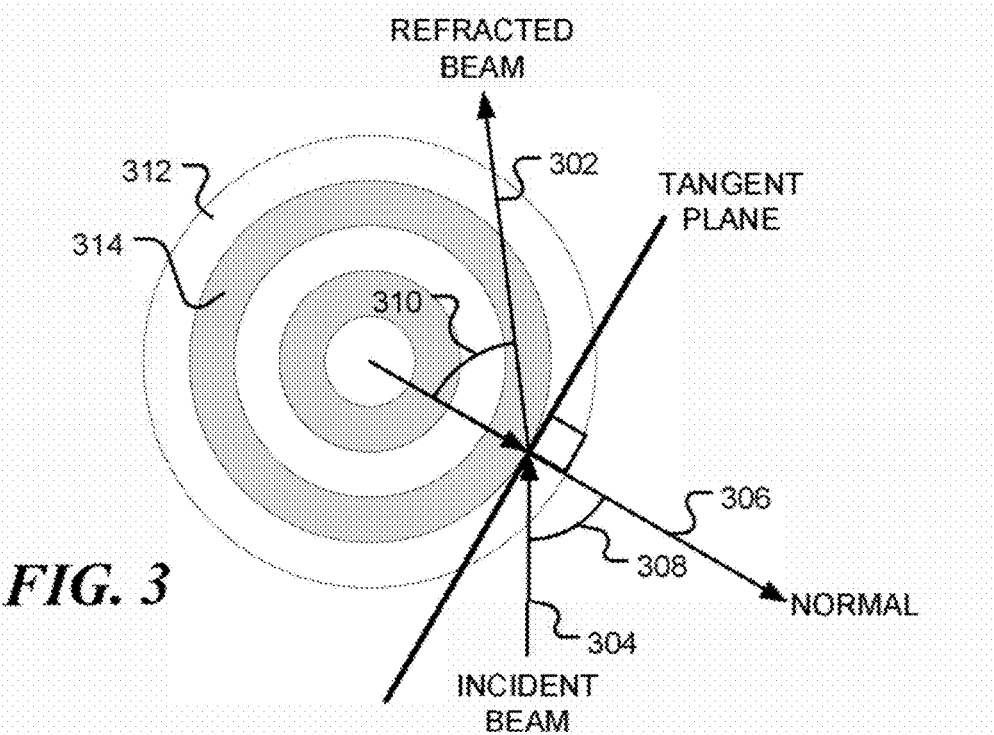
FIG. 3 illustrates the refraction of a probe beam as is passes through a region of varying refractive index due to an acoustic source.

FIG. 3 illustrates the refraction of a probe beam as is passes through a region of varying refractive index due to an acoustic source. Referring to FIG. 3, $v_{k+1}$ denotes the normalized vector of the refracted beam 302, $v_k$ denotes the normalized vector describing the direction of the incident beam 304. Vector $n_k$ 306 is the normalized plane vector. Angle $\theta_k$ 308 and angle $\theta_{k+1}$ 310, respectively, are the incidence and refraction angles at each side of the refractive index boundary. $n_k$ and $n_{k+1}$ are the refractive indices in regions 312 and 314, respectively, at each side of the boundary. The subscript k identifies the region. Normal vector $n_k$ 306 is defined as a line that intersects both the acoustic source origin and the point of intersection between incident ray $v_k$ and the wave front. While the regions of different refractive index are shown to be distinct in FIG. 3, the refractive index may be smoothly varying in practice.

The deflection of the probe beam as it intersects refractive index gradients or boundaries in the translucent medium is governed by Snell's law. In particular, the normalized propagation vector $v_{k+1}$ of the refracted beam is given by $$v_{k+1} = \frac{n_k}{n_{k+1}} v_k + \left( \cos\theta_{k+1} - \text{sgn}(n_k \cdot v_k) \frac{n_k}{n_{k+1}} \cos\theta_k \right) n_k. \quad (1)$$

In equation (1), $\text{sgn}(n_k \cdot v_k)$ denotes the sign of the dot product between the vectors $n_k$ and $v_k$ and $\theta_{k+1}$ denotes the angle of diffraction. The beam deflection vector is directly correlated to the angle of incidence $\theta_k$ of the beam at the refractive index boundary, and the vector n normal to the boundary. Therefore, the beam deflects in a direction correlated to the propagation direction of the acoustic wave.

PBDT ultrasound detection is based on the deflection of a laser beam resulting from refractive index gradients induced by acoustic waves. It is noted that the refractive indices $n_k$ and $n_{k+1}$ in regions 312 and 314 are dependent upon the strength of the ultrasound. As a result, the amplitude (and sign) of the deflection is dependent upon the strength of the ultrasound, causing motion of the deflected probe beam across the face of the deflection detector. However, the angle of the deflection depends only on the propagation direction.

Figure 4:
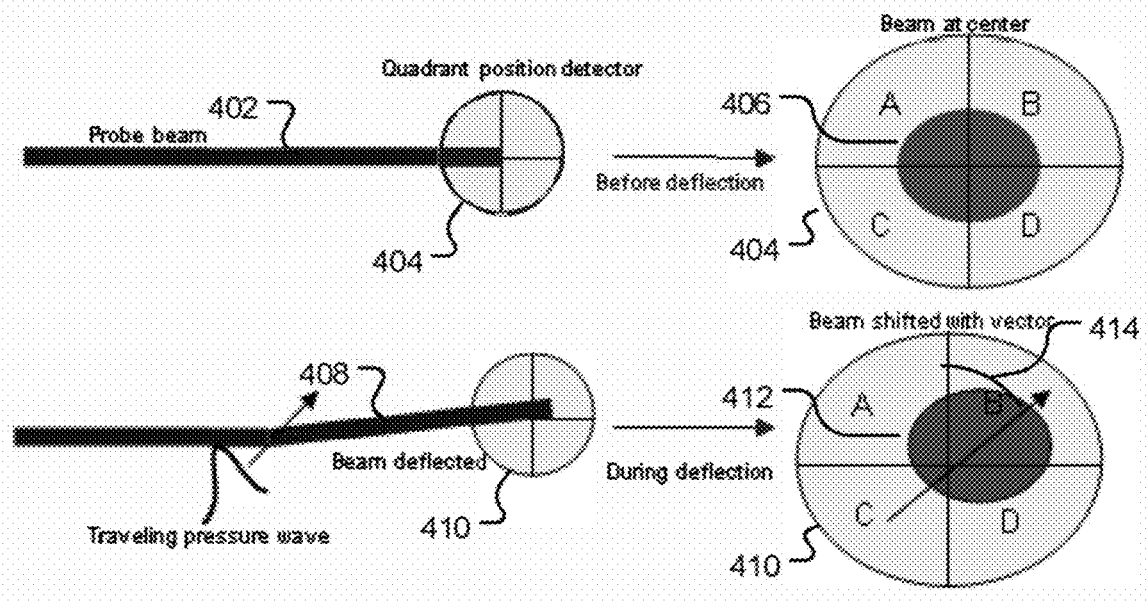
FIG. 4 illustrates operation of a probe beam deflection detector in accordance with a representative embodiment.

In one embodiment, the deflection of the laser beam is measured with a quadrature photodiode, although other detectors may be used. The motion of the beam across the quadrature photodiode face is translated into differential voltage signals. A diagram of probe beam/acoustic interaction and deflection detection with a quadrature photodiode is shown in FIG. 4. The upper diagram in FIG. 4 shows a beam 402 incident on a deflection detector 404. In this embodiment, the deflection detector 404 is a quadrature photodiode. Quadrature photodiode 404 comprises four regions indicated as A, B, C and D. The angle of beam deflection $\phi$ is resolved via two signals acquired from the quadrature photodiode (X,Y). Denoting a, b, c and d as the signals from detector regions A, B, C and D, respectively, first and second components of the signal are given by:

$$X = \frac{(a+c)-(b+d)}{a+b+c+d}, \quad Y = \frac{(a+b)-(c+d)}{a+b+c+d}. \quad (2)$$

The beam deflection angle $\phi$, shown as 414 in FIG. 4, satisfies $$\tan\phi = \frac{Y}{X}. \quad (3)$$

In the upper diagram, the beam 402 excites region 406 of quadrature photodiode 404. The beam is not deflected and so the region is centrally located. All four detector signals are equal and the resulting beam deflection angle, given by expression (3), is zero. In the lower diagram, the beam 408 is deflected before hitting detector 410 in region 412. The resulting detector signals a, b, c and d are unequal, resulting in a non-zero beam deflection angle.

Figure 5:
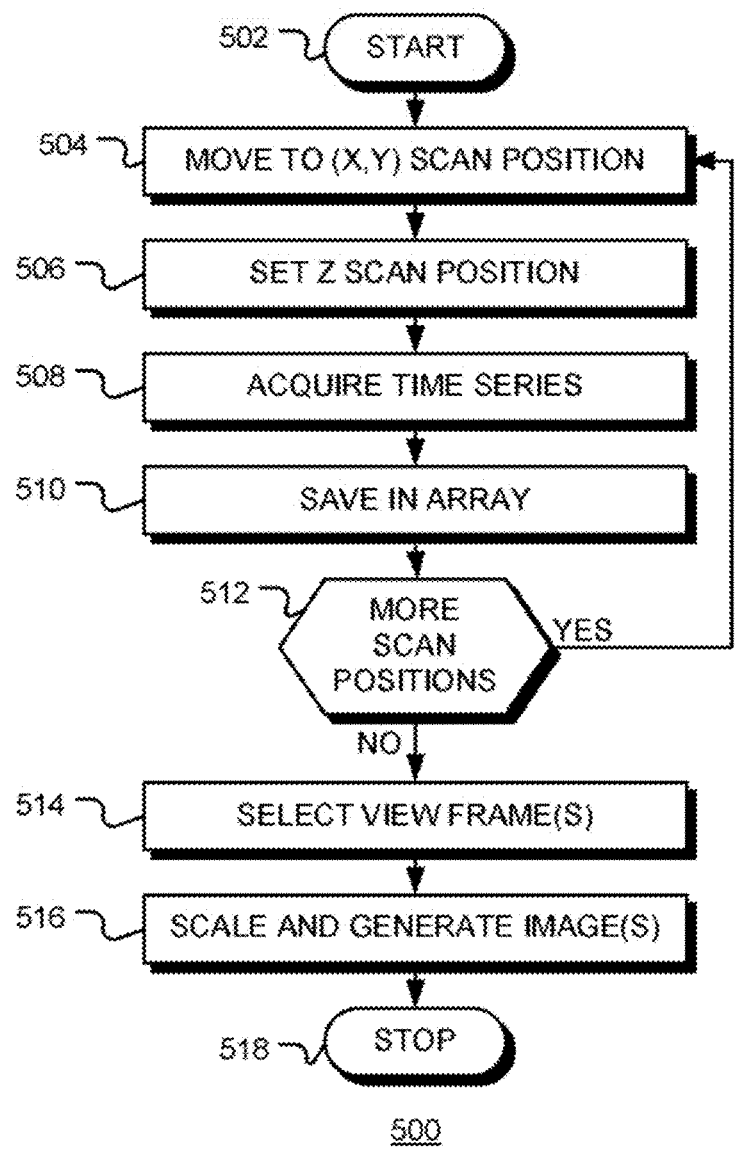
FIG. 5 is a flow chart of a method for generating an image, in accordance with a representative embodiment.

FIG. 5 is a flow chart of a method 500 for generating an image consistent with embodiments of the disclosure. Following start block 502, a probe beam is moved to a new scan position at block 504. Here, the position (X,Y) is assumed to be in a horizontal plane, but other geometries may be used. The probe beam may be moved by an X,Y scan stage for example. At block 506, the vertical (Z) location of the focus of the probe beam is adjusted. This may be done by a Z scan stage or by adjusting the focal length of the lens system, for example. At block 508, one or more time series are acquired from the beam deflection sensor. For example, a quadrature phase detector may provide 4 signals or 2 different signals. Optionally, an intensity signal from a polarization sensor may also be acquired. At block 510, the acquired signals, or signals derived from them, are stored in an array in a memory of the image processing module. The array may be indexed by {X, Y, Z, t}. Lower dimensional scans may be performed, resulting in {X, Y, t} or {X, Z, t} signal arrays, for example. If there are more scan points in the scan path or pattern, as depicted by the positive branch from decision block 512, flow returns to block 504. At each change of scan location one or more of the X, Y and Z coordinates in changed.

When all scan positions have been scanned, as depicted by the negative branch from decision block 512, a two-dimensional view frame is selected for generating an image at block 514. For example, a B-scan or B-mode image may be formed in an {X, t} or {Z, t} frame, or a C-scan or M-mode image may be formed in an {X, Y} or {X, Z} frame. The image is generated at block 516. The image displays the signal values at each position in the selected frame. They may be displayed in various forms such as a color map, brightness map, grayscale map, contour map, or 3-dimensional surface map, for example. In addition, multiple frames may be displayed in sequence in the form of a time-lapse series of frames or moving pictures. The method terminates at block 518

For each full scan range, a frame may be constructed with dimensions equivalent to scan range. For example, if a scan was 100 steps along the X-axis and 150 steps along the Y-axis, the dimensions of the frame might be a 100×150 array consisting of 15,000 beam positions. For each temporal step of the 1-D signal acquired at each scan location, a frame is created. For example, if the signals are recorded from 0 μs to 25 μs, with 50,000 temporal steps, the resulting time-lapse series of frames would consist of 50,000 frames of size 100×150 with each frame representing 500 picoseconds.

Figure 6:
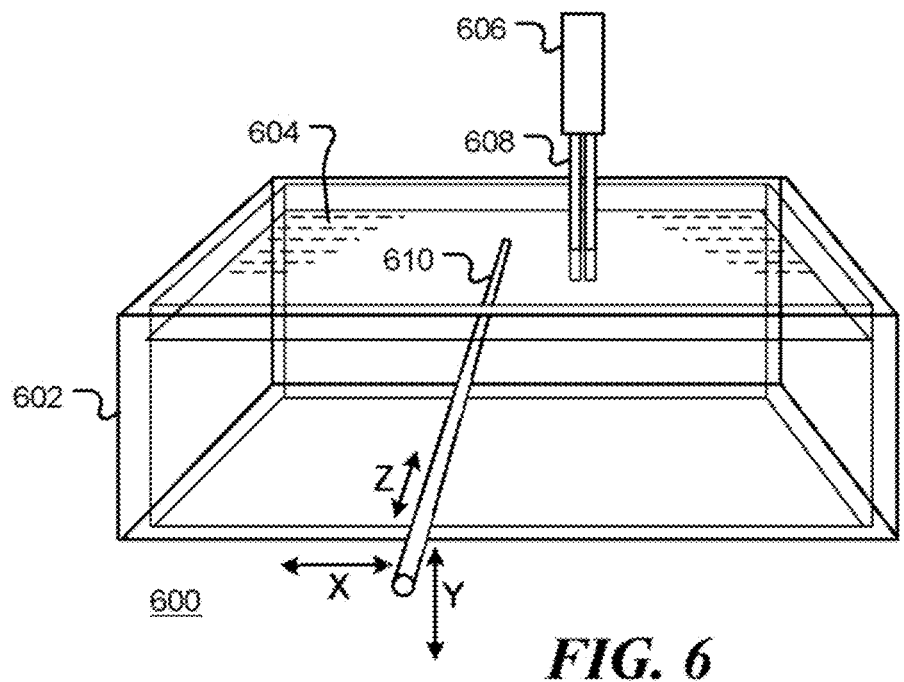
FIG. 6 illustrates scanning of a probe beam, in accordance with a representative embodiment.

FIG. 6 illustrates scanning of a probe beam, in accordance with a representative embodiment. System 600 includes a transparent tank 602 that contains the translucent medium 604 to be imaged. In the embodiment shown, energy element 606 supplies an electrical signal, such as a nanosecond electric pulse (nsEP), to electrodes 608. The electrodes excite the translucent medium 604 causing both mechanical (acoustic) and electromagnetic responses in the medium. The mechanical (acoustic) and electromagnetic responses cause deflections and polarization shifts in probe beam 610. In operation, probe beam 610 is positioned at a scan location in the X and Y directions, the electrodes are energized and the responses to a pulse are recorded. Probe beam 610 may be focused on a location in the translucent medium to enable scanning in a Z-direction, orthogonal to the X- and Y-directions. The Z-direction is along the axis of propagation of probe beam 610.

Translucent medium 604 may be excited by other energy elements, such as directed energy elements.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled, or executed to run on one of the above devices, as well as heterogeneous combinations of processors, processor architectures, or combinations of different hardware and software. In another implementation, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another implementation, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared or other device or combination of devices. In another implementation, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the scope of this disclosure and are intended to form a part of the disclosure as defined by the following claims, which are to be interpreted in the broadest sense allowable by law.

The various representative embodiments, which have been described in detail herein, have been presented by way of example and not by way of limitation. It will be understood by those skilled in the art that various changes may be made in the form and details of the described embodiments resulting in equivalent embodiments that remain within the scope of the appended claims.

What is claimed is:

1. An apparatus comprising:
   a probe beam generator configured to generate a probe beam;
   a first polarizing filter positioned between the probe beam generator and a translucent medium and configured to polarize the probe beam in a first direction perpendicular to a direction of propagation of the probe beam;
   a beam splitter positioned to receive the probe beam after it has been transmitted through the translucent medium, the beam splitter operable to split the received probe beam into a first split beam and second split beam;
   a probe beam deflection detector that receives the first split beam and is configured to provide one or more deflection signals in response to deflections of the first split beam associated with a refractive index variation in the translucent medium;

a second polarizing filter that receives the second split beam and is oriented to polarize the second split beam in a second direction, perpendicular to the first direction and perpendicular to the direction of propagation of the probe beam; and an intensity sensor that receives the second split beam after it has passed through the second polarizing filter, where intensity sensor provides an intensity signal associated with a polarization shift in the translucent medium.

2. The apparatus of claim 1, where the probe beam generator comprises:
a light source; and
a lens that focuses light from the light source at a first location.

3. The apparatus of claim 2, where the first location comprises a scan location of a plurality of scan locations of a scan pattern, the apparatus further comprising an image processing module operable to produce an image of spatial variations in the translucent medium dependent upon the plurality of scan locations.

4. The apparatus of claim 2, where the light source comprises a continuous wave (CW) light source.

5. The apparatus of claim 2, further comprising:
a scan stage having one or more degrees of positional freedom, the scan stage operable to move the first location in a scan pattern comprising one or more scan locations; and
an image processing module operable to produce an image of spatial variations in the translucent medium dependent upon the one or more scan locations.

6. The apparatus of claim 2, where the one or more degrees of positional freedom include a direction along the axis of the probe beam.

7. The apparatus of claim 2, further comprising a control module configured to vary a focal length of the lens so as to move the first location in a scan pattern.

8. The apparatus of claim 1, further comprising an image processing module operable to produce an image of temporal or spatial variations in the translucent medium dependent upon the one or more deflection signals, the intensity signal, or both the one or more deflection signals and the intensity signal.

9. The apparatus of claim 1, further comprising an energy element operable to excite the translucent medium and cause variations therein.

10. An apparatus comprising:
a probe beam generator, comprising a light source and a lens system, configured to generate a probe beam focused at a first location; and
a probe beam deflection detector that receives the probe beam and is configured to provide one or more deflection signals in response to deflections of the probe beam associated with a refractive index variation in a translucent medium located between the probe beam generator and the probe beam deflection detector;
a first polarizing filter positioned between the probe beam generator and the translucent medium and configured to polarize the probe beam in a first direction;
a beam splitter positioned to receive the probe beam after it has been transmitted through the translucent medium, the beam splitter operable to split the received probe beam into a first split beam and second split beam;
a second polarizing filter that receives the second split beam and is oriented to polarize the second split beam in a second direction, perpendicular to the first direction; and an intensity sensor that receives the second split beam after it has passed through the second polarizing filter, where intensity sensor provides an intensity signal associated with a polarization shift in the translucent medium,
where the probe beam deflection detector receives the first split beam.

11. The apparatus of claim 10, further comprising an energy element operable to excite the translucent medium and cause variations therein.

12. The apparatus of claim 10, further comprising:
a scan stage having one or more degrees of positional freedom, the scan stage operable to move the translucent medium or the probe beam in a scan pattern comprising one or more scan locations; and
an image processing module operable to produce an image of spatial variations in the translucent medium dependent upon the one or more scan locations.

13. A method for imaging variations in a translucent medium to provide an image, the method comprising:
for each scan location of a scan pattern comprising one or more scan locations:
focusing a probe beam at the scan location in the translucent medium; and
for each scan location of the scan pattern and for each sample time of a sampling duration comprising one or more sample times:
sensing deflection of the probe beam after it has been transmitted through the translucent medium;
assigning a position of a pixel in a first image dependent upon the scan location and the sample time; and
assigning a value to the pixel in the first image dependent upon the sensed deflection of the probe beam.

14. The method of claim 13, further comprising, at each scan location and each sample time:
passing the probe beam through a first polarizing filter positioned on one side of the translucent medium, the first polarizing filter configured to polarize the probe beam in a first direction;
passing the probe beam through a second polarizing filter positioned between the translucent medium and an intensity sensor, the second polarizing filter configured to polarize the probe beam in a second direction, perpendicular to the first direction;
sensing, by the intensity sensor, an intensity of the probe beam after passing through the second polarizing filter;
assigning a position of a pixel in a second image dependent upon the scan location, the sample time or both the scan location and the sample time; and
assigning a value of the pixel in the second image dependent upon the sensed polarization shift in the probe beam transmitted through the translucent medium.

15. The method of claim 13, further comprising exciting variations in the translucent medium using an energy element.

16. The method of claim 13, where focusing the probe beam at the scan location comprises passing a laser beam through a lens system comprising one or more lenses.

17. The method of claim 16, further comprising:
adjusting a focus of the lens system to move from a first scan location of the scan pattern to a second scan location of the scan pattern.

18. The method of claim 16, further comprising:
moving the lens system by a scan stage to move from a first scan location of the scan pattern to a second scan location of the scan pattern.

19. The method of claim 16, further comprising:
moving the translucent medium by a scan stage to move from a first scan location of the scan pattern to a second scan location of the scan pattern.

20. A method for sensing variations in a translucent medium, the method comprising:
transmitting a probe beam through the translucent medium;
detecting deflection of the probe beam after transmission through the translucent medium, the deflection associated with refractive index variations in the translucent medium; and
detecting a polarization shift in the probe beam after transmission through the translucent medium, the polarization shift associated with polarization variations in the translucent medium.

21. The method of claim 20, where detecting the polarization shift in the probe beam comprises:
transmitting the probe beam through a first polarizing filter positioned on one side of the translucent medium, the first polarizing filter configured to polarize the probe beam in a first direction;
passing the transmitted probe beam through a second polarizing filter positioned between the translucent medium and an intensity sensor, the second polarizing filter configured to polarize the probe beam in a second direction, perpendicular to the first direction; and
sensing, by the intensity sensor, the intensity of the probe after passing through the second polarization filter.

* * * * *